United States Patent
Banda et al.

(10) Patent No.: US 6,479,664 B1
(45) Date of Patent: Nov. 12, 2002

(54) PROCESS FOR THE PREPARATION OF 2-CHLORO-5-METHYLPYRIDINE-3-CARBALDEHYDE

(75) Inventors: Gangadasu Banda, Andhra Pradesh (IN); Chinaraju Bhimapaka, Andhra Pradesh (IN); Vaidya Jayathirtha Rao, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/098,523

(22) Filed: Mar. 18, 2002

(51) Int. Cl.[7] ............................................. C07D 213/12
(52) U.S. Cl. ...................................................... 546/315
(58) Field of Search .......................................... 546/315

(56) References Cited

U.S. PATENT DOCUMENTS 5,708,180 A * 1/1998 Beck et al. .................. 546/315

FOREIGN PATENT DOCUMENTS

EP          0 702 003 A3       3/1996
EP          0 702 003 A2       3/1996

OTHER PUBLICATIONS

Cohn et al., "A Versatile New Synthesis of Quinoline and Related Fused Pyridines. Part 12. [1]A General Synthesis of 2–Chloropyridines and 2–Pyridones", J. Chem. Soc. Perkin Trans. 1, 1984, pp. 1173–1182.

* cited by examiner

*Primary Examiner*—Patricia L. Morris
(74) *Attorney, Agent, or Firm*—Burns, Doane, Swecker & Mathis, L.L.P.

(57) ABSTRACT

The present invention describes an improved process for the preparation of 2-chloro-5-methylpyridine-3-carbaldehyde from N-benzyl-N-(1-Propenyl)acetamide using diphosgene and dimethylformamide or triphosgene and dimethylformamide (Vilsmeyer reagent) in 92% yield against reported 12% yield. The present invention has the advantage of using diphosgene and triphosgene instead of toxic phosgene gas and phosphorousoxytrichloride, thereby avoiding the formation of phosphorous salt.

6 Claims, No Drawings

PROCESS FOR THE PREPARATION OF 2-CHLORO-5-METHYLPYRIDINE-3-CARBALDEHYDE

FIELD OF THE INVENTION

The present invention relates to a process for the preparation of 2-chloro-5-methylpyridine-3-carbaldehyde, a useful intermediate for the variety of pharmaceutical and pesticide products. The present invention particularly relates to a process for the preparation of 2-chloro-5-methylpyridine-3-carbaldehyde of formula 1 given below using diphosgene and triphosgene.

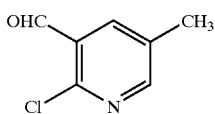

Formula 1

The present invention also relates to a process for the preparation of 2-chloro-5-methyl-pyridine-3-carbaldehyde under suitable conditions of mole ratio, time and temperature with high selectivity.

BACKGROUND OF THE INVENTION

Several pyridine, quinoline and isoquinoline compounds are important intermediates in that they have been reported as potential anti tumor agents (J. Med. Chem, 19, 1209, 1976; CA 85: 116544q). Carbaldehyde based products served as ulcer healing agents (Ger. Offen DE 3324034, 1984; CA 101:54936g), allergy inhibitors (EP 120483, 1984; CA 102:95649e; EP120484, 1984; CA 102:113500f), antiviral agents (CA 113:172015b), and useful as intermediates for pharmaceuticals (Ger. Offen DE 4429465, 1996; CA 124:343116u).

Substituted pyridine carbaldehyde is an important compound to prepare the amlexanox a drug which is useful for treatment of mucosites and in the treatment of aphthous ulcers (Drgs of the future 25(5), 511,200).

Chloropyridinecarbaldehyde is a very useful intermediate to make various compounds like sulfones and vinyl pyridines in organic syntheses (Heterocyclic Commun, 5(3), 257,1999) 1,2,3,4-tetrahydrodibenzo-1,8-naphthyridines are prepared from 2-chloro-3-formyl quinolines (Hetero-cyclic Commun. 6(1),63,2000).

There is only one method appeared in the literature for the preparation of 2-chloro-5-methylpyridine-3-carbaldehyde in 12% yield (J. C. S. Perkin Trans. 1,1173, 1984).

OBJECTS OF THE INVENTION

The main object of the invention is to provide an improved method for the preparation of 2-chloro-5-methylpyridine-3-carbaldehyde in improved yield.

It is another object of the invention to provide an improved method for the preparation of 2-chloro-5-methylpyridine-3-carbaldehyde with shorter reaction times and suitable temperatures.

It is another object of the invention to provide an improved method for the preparation of 2-chloro-5-methylpyridine-3-carbaldehyde wherein product isolation is very easy.

It is another object of the invention to provide an improved method for the preparation of 2-chloro-5-methylpyridine-3-carbaldehyde using easily handled non-toxic diphosgene and triphosgene.

SUMMARY OF THE INVENTION

The present invention describes an improved process for the preparation of 2-chloro-5-methylpyridine-3-carbaldehyde from N-benzyl-N-(1-Propenyl) acetamide using diphosgene and dimethylformamide or triphosgene and dimethylformamide (Vilsmeyer reagent) in 92% yield against reported 12% yield. The present invention has the advantage of using diphosgene and triphosgene instead of toxic phosgene gas and phosphorousoxytrichloride, thereby avoiding the formation of phosphorous salt.

Accordingly the present invention provides a process for the preparation of 2-chloro-5-methylpyridine-3-carbaldehyde of the formula 1 below

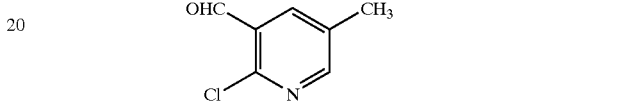

Formula 1 comprising reacting N-benzyl-N-(1-Propenyl) acetamide with a reagent selected from dimethylformamide mixed with diphosgene or triphosgene (Vilsmeyer reagent) under dry conditions at a temperature in the range of 75–100° C.

In another embodiment of the invention, the reaction is carried out for a time period in the range of 4–16 hours.

In another embodiment of the invention, the mole ratio of dimethylformamide to diphosgene or triphosgene is in the range of 1:1–2.

In a further embodiment of the invention, the mole ratio of dimethylformamide to diphosgene is in the range of 1:1–2.

In a further embodiment of the invention, the mole ratio of dimethylformamide to triphosgene is 1:1.

In a further embodiment of the invention, N-benzyl-N-(1-Propenyl)acetamide and reagent are mixed before heating in an ice cold bath.

In another embodiment of the invention, the mole ratio of diphosgene and triphosgene with dimethylformamide is critical to the formation of the formylating reagent and subsequent formation of the cyclised product leading to 2-chloro-5-methylpyridine-3-carbaldehyde.

DETAILED DESCRIPTION OF THE INVENTION

The following examples are given by way of illustration of the present invention and there fore should not be construed to the scope of the present invention.

EXAMPLE 1

Dimethylformamide (13.54 g, 0.185 moles) was added to a well stirred and cooled material of diphosgene (36.64 g, 0.185 moles) at 4° C. in 30 minutes in an ice bath followed by N-benzyl-N-(1-Propenyl)acetamide (5 g, 0.026 moles) at the same temperature. The reaction mixture was further continued for 2 hours at 25° C. The ice cold bath was removed and heated to 75° C. for 5 hours. The orange-yellow coloured organic mass was poured in ice cold water (200 g) with stirring. The mass was extracted with methylenechloride (2×200 ml) and the layer was separated. The organic layer was dried over sodium sulfate, and the solvent was removed under reduced pressure. The obtained residue was subjected to chromatographic purification on silica gel to give 2-chloro-5-methylpyridine-3-carbaldehyde (3.78 g) in 92% yield.

EXAMPLE 2

Dimethylformamide (13.54 g, 0.185 moles) was added to a well stirred and cooled material of diphosgene (36.64 g, 0.185 moles) at 10° C. in 30 minutes in an ice bath followed by N-benzyl-N-(1-Propenyl)acetamide (5 g, 0.026 moles) at the same temperature. The reaction mixture was further continued for 2 hours at 25° C. The ice cold bath was removed and heated to 75° C. for 5 hours. The orange-yellow coloured organic mass was poured in ice cold water (200 g) with stirring. The mass was extracted with methylenechloride (2×200 ml) and the layer separated. The organic layer was dried over sodium sulfate, and solvent removed under reduced pressure. Residue obtained was subjected to chromatographic purification on silica gel to give 2-chloro-5-methylpyridine-3-carbaldehyde (3.78 g) in 92% yield.

EXAMPLE 3

Dimethylformamide (19.34 g, 0.264 moles) was added to a well stirred and cooled material of diphosgene (36.64 g, 0.185 moles) at 4° C. in 30 minutes in an ice bath followed by N-benzyl-N-(1-Propenyl)acetamide (5 g, 0.026 moles) at the same temperature. The reaction mixture was further continued for 2 hours at 30° C. The ice cold both was removed and heated to 75° C. for 8 hours. Work up procedure was carried out according to the procedure of example 1. Before that excess DMF was removed under reduced pressure. The obtained residue was subjected to chromatographic purification on silica gel to give 2-chloro-5-methylpyridine-3-carbaldehyde (3.78 g) in 92% yield.

EXAMPLE 4

Dimethylformamide (19.34 g, 0.264 moles) was added to a well stirred and cooled material of diphosgene (36.64 g, 0.185 moles) at 10° C. in 30 minutes in an ice bath followed by N-benzyl-N-(1-Propenyl)acetamide (5 g, 0.026 moles) at the same temperature. The reaction mixture was further continued for 2 hours at 30° C. The ice cold both was removed and heated to 75° C. for 8 hours. Work up procedure was carried out according to the procedure of example 1. Before that excess DMF was removed under reduced pressure. The obtained residue was subjected to chromatographic purification on silica gel to give 2-chloro-5-methylpyridine-3-carbaldehyde (3.78 g) in 92% yield.

EXAMPLE 5

Dimethylformamide (2.71 g, 0.037 moles) was added to a well stirred and cooled material of triphosgene (10.99 g, 0.037 moles) at 4° C. in 30 minutes in an ice bath followed by N-benzyl-N-(1-Propenyl)acetamide (1 g, 0.005 moles) at the temperature. The reaction mixture was further continued for 2 hours at 25° C. The ice cold bath was removed and heated to75° C. for 5 hours. Work up procedure was carried out according to the procedure of example 1. The obtained residue was subjected to chromatographic purification on silica gel to give 2-chloro-5-methylpyridine-3-carbaldeyde in 92% yield.

EXAMPLE 6

Dimethylformamide (13.54 g, 0.185 moles) was added to well stirred and cooled material of triphosgene (55 g, 0.185 moles) at 4° C. in 30 minutes in an ice bath followed by N-benzyl-N-(1-Propenyl)acetamide (5 g, 0.02645 moles) at the same temperature. The reaction mixture was further continued for 2 hours at 25° C. The ice cold bath was removed and heated to 75° C. for 5 hours. The work up procedure was carried out according to the above mentioned procedure. The obtained residue was subjected to chromatographic purification on silica gel to give 2-choloro-5-methylpyridine-3-carbaldehyde in 92% yield.

ADVANTAGES

High yield of 2-choloro-5-methylpyridine-3-carbaldehyde has been obtained for the first time.

The advantage of the present invention is the employment of controlled time and temperature conditions during the reaction which are critical to the formation of the reagent and the product.

The another advantage of the present invention that it requires shorter reaction times and suitable temperatures.

Another advantage of the present invention is that the product isolation is very easy.

Yet another advantage of the present invention is that the handling of diphosgene and triphosgene are very easy when compared to toxic phosgene gas.

We claim:

1. A process for the preparation of 2-chloro-5-methylpyridine-3-carbaldehyde of the formula 1 below

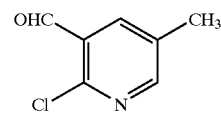

Formula 1 comprising reacting N-benzyl-N-(1-Propenyl)acetamide with a reagent selected from dimethylformamide mixed with diphosgene or triphosgene (Vilsmeyer reagent) under dry conditions at a temperature in the range of 75–100° C.

2. A process as claimed in claim 1 wherein the reaction is carried out for a time period in the range of 4–16 hours.

3. A process as claimed in claim 1 wherein the mole ratio of dimethylformamide to diphosgene or triphosgene is in the range of 1:1–2.

4. A process as claimed in claim 3 wherein the mole ratio of dimethylformamide to diphosgene is in the range of 1:1–2.

5. A process as claimed in claim 3 wherein the mole ratio of dimethylformamide to triphosgene is 1:1.

6. A process as claimed in claim 1 wherein the N-benzyl-N-(1-Propenyl)acetamide and reagent are mixed before heating in an ice cold bath.

* * * * *